US006704935B1

(12) United States Patent
MacDonald

(10) Patent No.: US 6,704,935 B1
(45) Date of Patent: Mar. 16, 2004

(54) CLEAR TANNING GLASSES WITH OPAQUE EYEPIECES

(76) Inventor: Shelly A. MacDonald, 128 Koebrick La., Camp Verde, AZ (US) 86322

( * ) Notice: Subject to any disclaimer, the term of this patent is extended or adjusted under 35 U.S.C. 154(b) by 0 days.

(21) Appl. No.: 10/252,163

(22) Filed: Sep. 23, 2002

(51) Int. Cl.[7] ................................................. A61F 9/00
(52) U.S. Cl. ............................................... 2/15; 351/41
(58) Field of Search ....................... 2/454, 15; 128/858; 351/41, 45

(56) References Cited

U.S. PATENT DOCUMENTS

| 589,307 | A | | 8/1897 | Seffer | |
|---|---|---|---|---|---|
| 900,444 | A | | 10/1908 | Stickle | |
| 2,572,638 | A | | 10/1951 | Loos | |
| 2,642,569 | A | * | 6/1953 | Triebes et al. | 351/46 |
| 4,068,918 | A | * | 1/1978 | Holcombe, Jr. | 359/358 |
| 4,162,542 | A | | 7/1979 | Frank | |
| 4,411,263 | A | | 10/1983 | Cook | |
| 4,502,476 | A | | 3/1985 | Welt | |
| D285,624 | S | | 9/1986 | Rosenbaum | |
| 4,848,889 | A | * | 7/1989 | Shaw | 351/51 |
| 5,307,523 | A | | 5/1994 | Lewis et al. | |
| 5,528,773 | A | * | 6/1996 | Lowinger | 2/161.4 |
| D374,950 | S | | 10/1996 | Clark | |
| 6,131,208 | A | | 10/2000 | Banks | |
| 2002/0157165 | A1 | * | 10/2002 | Kroll et al. | 2/69 |
| 2003/0056281 | A1 | * | 3/2003 | Hasegawa | 2/428 |

* cited by examiner

Primary Examiner—John J. Calvert
Assistant Examiner—Katherine Moran
(74) Attorney, Agent, or Firm—Randal D. Homburg

(57) ABSTRACT

The tanning glasses comprising this invention include a transparent glasses frame, including a nosepiece, collapsible earpieces and lenses, but combines a hook and loop fastening material crossing the lenses in front of the eyes to which two molded and opaque eye cups, adapted to cover the eyes and fitted to the eye sockets of the wearer, having attached corresponding hook and loop fastening material, attach to the hook and loop fastening material on the lenses, adjustable to fit the distinctly different location of the eye sockets on a variety of wearers faces. When worn by a user, the eyepieces over the eyes preventing damage to the eyes from exposure to light, either artificial or natural.

2 Claims, 2 Drawing Sheets

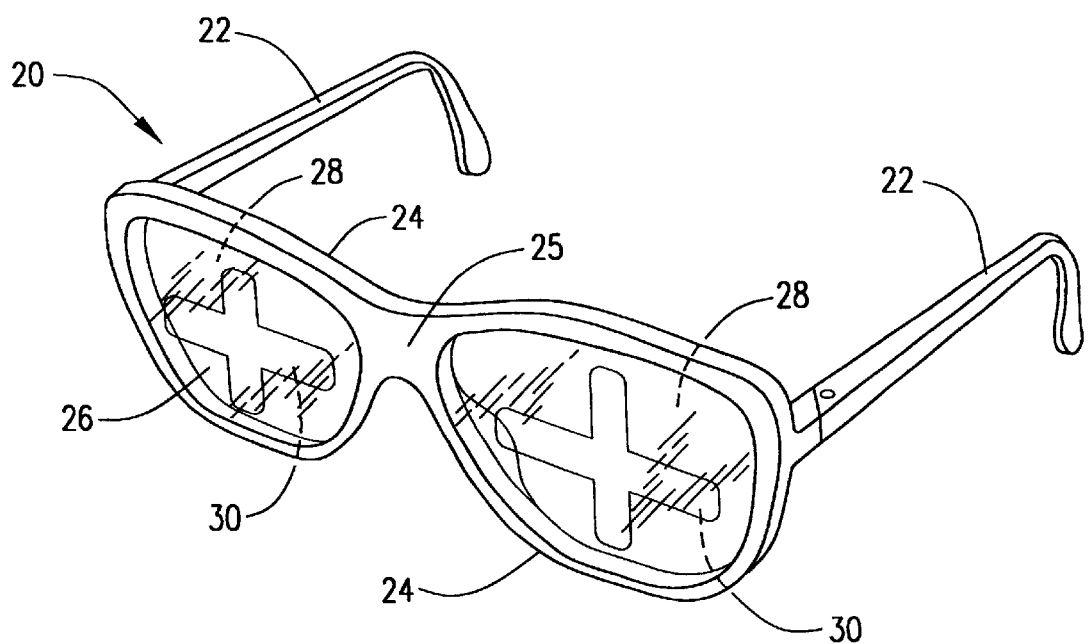
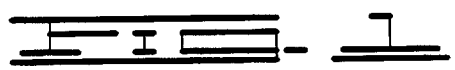
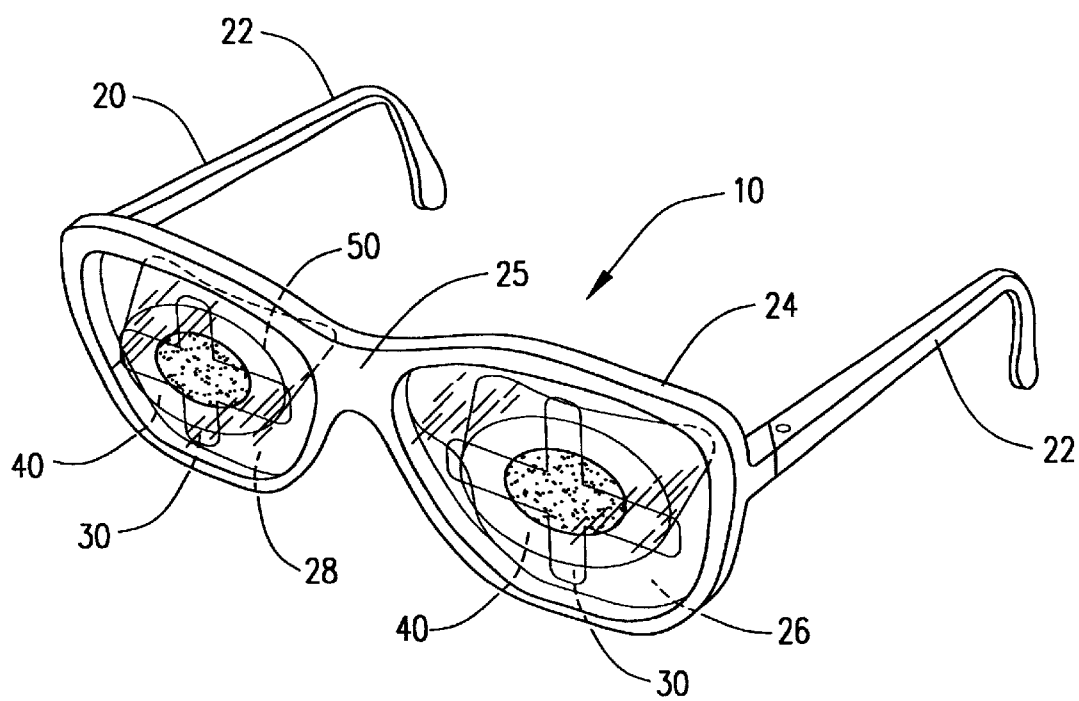
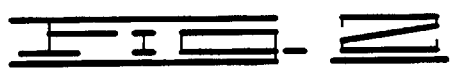

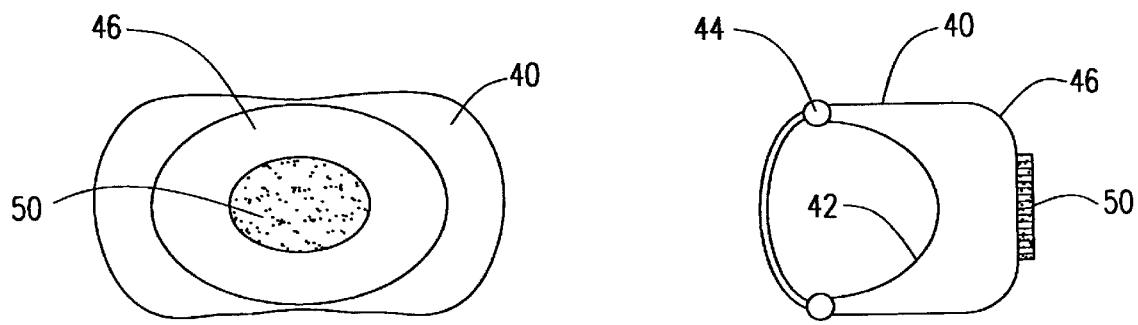
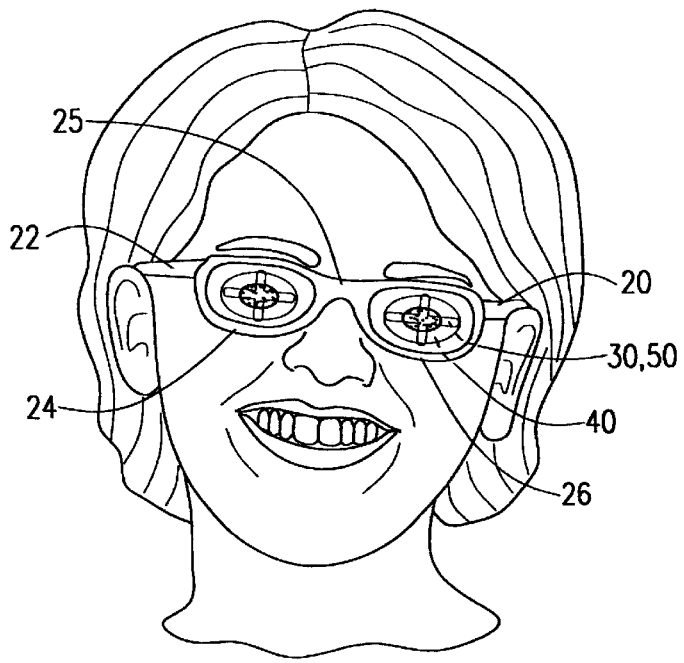
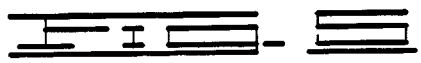

CLEAR TANNING GLASSES WITH OPAQUE EYEPIECES

CROSS REFERENCE TO RELATED APPLICATIONS

None

BACKGROUND OF THE INVENTION

1. Field of Invention

The tanning glasses comprising this invention include a transparent glasses frame, including a nosepiece, collapsible earpieces and lenses, but combines a hook and loop fastening material crossing the lenses in front of the eyes to which two molded and opaque eye cups, adapted to cover the eyes and fitted to the eye sockets of the wearer, having attached corresponding hook and loop fastening material, attach to the hook and loop fastening material on the lenses, adjustable to fit the distinctly different location of the eye sockets on a variety of wearers faces. When worn by a user, the eyepieces over the eyes preventing damage to the eyes from exposure to light, either artificial or natural.

2. Description of Prior Art

The following United States patents were discovered and are disclosed within this application for utility patent. All relate to eye covering devices to protect the wearer from light.

Two design patents disclosing apparent complete light blocking eyewear are disclosed in U.S. Design Pat. No. D 285,624 to Rosenbaum and U.S. Pat. No. D 374,950 to Clark. Two patents located, U.S. Pat. No. 2,572,638 to Loos and U.S. Pat. No. 6,131,208 to Banks, show devices that merely adhere to the eye sockets of the user, completely or substantially covering the eyes of the user. A covering used over glasses or spectacles is disclosed in U.S. Pat. No. 900,444 to Stickle.

Infant eyewear for babies requiring exposure to ultraviolet light for medical purposes is disclosed in U.S. Pat. No. 4,502,476 to Welt and U.S. Pat. No. 4,411,263 to Cook, with Cook having an adhesive attaching means to adhere the straps of the eyewear to the head of the infant wearer, while Welt includes banded headgear to secure the eyepieces to the head of the child using a first strap going over the top of the babies head a second strap going behind the babies head and the third strap, containing the eye covering, going across the babies face across the eye line.

Three U.S. Pat. No. 5,307,523 to Lewis, U.S. Pat. No. 4,656,668 to Castrejon, and U.S. Pat. No. 4,162,542 to Frank, disclose full and partial eye covering with a formed nose piece connecting the two eyepieces of each invention, also including an elastic strap. Lewis discloses a briefly described lens in a lens opening in the flat front of each eyepiece, without any disclosure of the purpose for the opening, other than inferring some sight through the lens. Lewis is also suggested as a singular molded piece with an elastic strap going around the head. The Frank '542 patent discloses the lenses as being tinted with a metallic outer coating, but having transparent nose pieces and head strap, generally used for skiing as a form of goggles.

U.S. Pat. No. 589,307 to Seffer, known as a hoodwink, is disclosed as a pair of eyepieces mounted on an elastic cord or web capable of longitudinal adjustment along the cord or web, to cover the eyes of the wearer, protecting the wearer from excluding flashes of lightning during an electrical storm, to obviate shocks, which are "so distressing to the nervous systems, especially of weak and delicate women."

None of the above inventions disclose a transparent frame, having a nosepiece, lenses, frames and earpieces folding from the frames, having a hook and loop fastening material on the lenses positioned to accept a hook and loop fastening material attached to the flattened outer surfaces of opaque elliptical eyepieces, having a concave inner surface, covering the eye area only without restriction of sunlight to the rest of the face, yet providing secure and adjustable fit to the wearer in any position.

SUMMARY OF THE INVENTION

The primary objective of the invention is to provide a secure tanning device with a clear support structure to which opaque and protective eyepieces are adjustably attached with a hook and loop material, positioning the eyepieces precisely upon the eye sockets of the wearer to completely shield the eyes of the wearer and remain in place regardless of the position of the wearer.

DESCRIPTION OF THE DRAWINGS

The following drawings are submitted with this utility patent application.

FIG. 1 is a perspective view of the glasses frame without the eyepieces.

FIG. 2 is a perspective view of the glasses frame including the eyepieces.

FIG. 3 is a front view of an eyepiece.

FIG. 4 is a side cross-section of an eyepiece.

FIG. 5 is a front view of the protective eyeglasses on the face of a user.

DESCRIPTION OF THE PREFERRED EMBODIMENT

The tanning glasses of the present invention are used to protect and cover the eyes of the wearer from exposure to harmful UV rays during tanning, without impeding the wearer from gaining a full facial tan, except for the eyes, the tanning glasses 10 comprising essentially a transparent set of frames 20, having transparent ear pieces 22 folding onto transparent lens supports 24 having a transparent nosepiece 25 and clear lenses 26 set within the lens supports 24, the lenses 26 having an inner surface 28 upon which a transparent hook and loop fastening material 30 is placed. Also included are a pair of flexible oval eyepieces 40, having an inner concave surface 42 with a soft lining 44 and a flat outer surface 46, each eyepiece adapted to fit an eye socket of a wearer, the outer flat surface 46 having a corresponding hook and loop fastening material 50, which may be removably attached to the transparent hook and look fastening material 30 on the inner surface 28 of the lenses 26 of the frames 20.

Initial application of the tanning glasses 10 to the wearer would include placing the eyepieces 40 on the eyes of the wearer and then placing the frames 20 on the wearer's head in a comfortable position, followed by gently pressing the nosepiece 25 of the frames 20 against the wearers face, engaging the hook and loop fastening material 50 on the flat outer surfaces 46 of the eyepieces 40 to the hook and loop fastening material 30 on the inner surface 28 of the lenses 20. After this initial application, the frames 20 and eyepieces 40 may be removed from the wearer's head multiple times, without having to repositioning the eyepieces 40. In the event another wearer desires to use the tanning glasses 10, as would be the case in a tanning salon, the eyepieces 40 may be removed from the lenses 26 and reapplied to the new wearer.

The frames 20 preferable are made of a clear acrylic material to minimize blockage of the ultraviolet light rays penetrating the frames 20, while the eyepieces 40 would be made of a rubberized flexible material, conforming more easily to the different eye socket shapes of the variety of wearers. Foam rubber in the shape of a ring may also serve as the soft lining 44 disclosed above.

While the invention has been particularly shown and described with reference to a preferred embodiment thereof, it will be understood by those skilled in the art that changes in form and detail may be made therein without departing from the spirit and scope of the invention.

What is claimed is:

1. A set of tanning glasses used to protect and cover the eyes of the wearer from exposure to harmful UV rays during tanning, without impeding the wearer from gaining an otherwise full facial tan the tanning glasses comprising:

a transparent set of frames, having transparent ear pieces folding onto transparent frames having a transparent nosepiece and clear lenses, the lenses having an inner surface upon which a transparent hook and loop fastening material is placed; and a pair of flexible oval eyepieces, having an inner concave surface with a soft lining and a flat outer surface, the outer flat surface having a hook and loop fastening material, removably attached to the transparent hook and loop fastening material on the inner surface of the lens of the frames.

2. The tanning glasses, as disclosed in claim 1, wherein:

the frames are made of a transparent acrylic material;

the eyepieces are made of a rubberized flexible material, and the soft lining is foam rubber.

\* \* \* \* \*